US010295526B2

(12) United States Patent
Rust et al.

(10) Patent No.: US 10,295,526 B2
(45) Date of Patent: May 21, 2019

(54) METHOD OF EVALUATING A HEMOCRIT

(71) Applicant: Western New England University, Springfield, MA (US)

(72) Inventors: Michael Rust, Springfield, MA (US); Joseph T. Papu, Port Jefferson Station, NY (US); Andrew w. Browne, Worthington, OH (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 345 days.

(21) Appl. No.: 15/006,326

(22) Filed: Jan. 26, 2016

(65) Prior Publication Data
US 2016/0139107 A1    May 19, 2016

Related U.S. Application Data

(62) Division of application No. 13/858,257, filed on Apr. 8, 2013, now abandoned.
(Continued)

(51) Int. Cl.
*A61M 1/36* (2006.01)
*B04B 5/02* (2006.01)
(Continued)

(52) U.S. Cl.
CPC ......... *G01N 33/491* (2013.01); *A61M 1/3693* (2013.01); *B04B 5/02* (2013.01);
(Continued)

(58) Field of Classification Search
CPC .......... B04B 5/02; B04B 5/0414; B04B 9/00; B04B 9/02; G01N 33/491; G01N 2015/055
(Continued)

(56) References Cited

U.S. PATENT DOCUMENTS 4,738,655 A * 4/1988 Brimhall ................. B04B 9/02
494/10
5,242,370 A * 9/1993 Silver ................... B01L 3/5021
422/918
(Continued)

FOREIGN PATENT DOCUMENTS

CN        200963974 Y  * 10/2007
WO      2007025096 A1    3/2007
WO   WO 2007025096 A1 *  3/2007  .............. B60L 8/003

OTHER PUBLICATIONS

Final Office Action for U.S. Appl. No 13/858,257 dated Oct. 6, 2015; 10 pages.
(Continued)

*Primary Examiner* — Walter D.. Griffin
*Assistant Examiner* — Shuyi S. Liu
(74) *Attorney, Agent, or Firm* — Cantor Colburn LLP (57) ABSTRACT

A centrifuge is provided. The centrifuge includes a power source, the power source configured to generate electrical power from a renewable power source. At least one battery electrically coupled to the power source. A motor is electrically coupled to the at least one battery. A rotor is coupled to the motor. The rotor has a generally cylindrical body and a pair of opposing openings opposite the motor, and a pair of holders each disposed in one of the pair of opposing openings, each of the holders having an opening on one end sized to receive a capillary tube.

7 Claims, 9 Drawing Sheets

Related U.S. Application Data (60) Provisional application No. 61/621,691, filed on Apr. 9, 2012.

(51) Int. Cl.
  *B04B 5/04* (2006.01)
  *B04B 9/00* (2006.01)
  *B04B 9/02* (2006.01)
  *G01N 33/49* (2006.01)

(52) U.S. Cl.
  CPC .............. *B04B 5/0414* (2013.01); *B04B 9/00* (2013.01); *B04B 9/02* (2013.01)

(58) Field of Classification Search
  USPC .................... 494/16, 20; 348/137; 73/61, 43
  See application file for complete search history.

(56) References Cited

U.S. PATENT DOCUMENTS

| | | | | |
|---|---|---|---|---|
| 5,840,019 | A * | 11/1998 | Wirebaugh | G09B 29/00 600/300 |
| 6,506,606 | B1 * | 1/2003 | Winkelman | G01N 15/042 422/72 |
| 2005/0051466 | A1 * | 3/2005 | Carter | B04B 13/00 210/94 |

OTHER PUBLICATIONS

Non Final Office Action for U.S. Appl. No. 13/858,257 dated Jun. 5, 2015; 59 pages.

* cited by examiner

METHOD OF EVALUATING A HEMOCRIT

CROSS REFERENCE TO RELATED APPLICATIONS

The present application is a divisional application of U.S. application Ser. No. 13/858,257 filed on Apr. 8, 2013, which is a nonprovisional application of U.S. Provisional Application Ser. No. 61/621,691 filed on Apr. 9, 2012, the contents of which is incorporated by reference herein in its entirety.

BACKGROUND

The subject matter disclosed herein relates to a centrifuge and in particular to a portable centrifuge for determining a patient's hematocrit.

Blood can be fractionated, and the different fractions of the blood can be used to diagnose a patient to determine their medical needs. Under the influence of gravity or centrifugal force, blood spontaneously sediments into three layers. At equilibrium, the top low-density layer is a straw-colored clear fluid called plasma. Plasma is a water solution of salts, metabolites, peptides, and many proteins ranging from small (insulin) to very large (complement components).

The bottom, high-density layer is a deep red viscous fluid composed of red blood cells (erythrocytes) specialized for oxygen transport. The relative volume of whole blood that consists of erythrocytes is called the hematocrit, and in normal human beings this can range from about 37% to about 52% of whole blood.

The intermediate layer is the smallest, appearing as a thin white band above the erythrocyte layer and below the plasma layer; this is called the buffy coat.

It is often desirable to check the patient's hematocrit to determine if the amount of red blood cells in the patient's blood is within normal ranges, or if it is low (anemic) or high (polycythemic). It may be desired to perform this analysis frequently to check the effectiveness of treatments or to determine a change in the patient's condition. The processing of blood typically requires significant capital investment in centrifugation equipment, lab space and skilled personnel to process the samples. It should be appreciated that it is often difficult to perform this analysis in areas where the local environment or infrastructure does not provide the economic resources for equipment or the skilled personnel needed to perform the analysis.

Accordingly, while existing centrifuges are suitable for their intended purposes the need for improvement remains, particularly in providing a centrifuge and system that can be used to check a patient's hematocrit in remote or low resource areas.

BRIEF DESCRIPTION OF EMBODIMENTS OF THE INVENTION

According to one aspect of the invention, a centrifuge is provided. The centrifuge includes a power source, the power source configured to generate electrical power from a renewable power source. At least one battery is electrically coupled to the power source. A motor is electrically coupled to at least one battery. A rotor is coupled to the motor, the rotor having a generally cylindrical body and a pair of opposing openings opposite the motor. A pair of holders are each disposed in one of the pair of opposing openings, each of the holders having an opening on one end sized to receive a capillary tube.

According to another aspect of the invention, a diagnosis card comprising a base member is provided. The base member includes a base line indicia. A lower normal line indicia is provided having a first starting point spaced apart from the base line, the lower normal line extending on an angle relative to the base line. An upper normal line indicia is provided having a second starting point coincident with the first starting point, the upper normal line extending on an angle relative to the lower normal line. A 100% level line indicia is provided having a third starting point spaced apart from the first starting point, the 100% level line extending on an angle relative to the upper normal line.

According to yet another aspect of the invention, a method of evaluating a patient's hematocrit is provided. The method includes separating a sample of blood in a capillary tube into a red blood cell portion and a plasma portion, the capillary tube having a bottom end. A diagnosis card is provided having a base line indicia. a lower normal line indicia, an upper normal line indicia and a 100% level line. The lower normal line indicia includes a first starting point spaced apart from the base line, the lower normal line extending on an angle relative to the base line. The upper normal line indicia includes a second starting point coincident with the first starting point, the upper normal line extending on an angle relative to the lower normal line. The 100% level line indicia having a third starting point spaced apart from the first starting point, the 100% level line extending on an angle relative to the upper normal line. The capillary tube is placed against the diagnosis card with the bottom end placed adjacent the base line.

According to yet another aspect of the invention, a system for evaluating a patient's hematocrit in a low resource area is provided. The system includes a centrifuge. The centrifuge includes a solar panel, at least one battery electrically coupled to the solar panel, a motor electrically coupled to at least one battery, and a rotor coupled to the motor. The rotor has a generally cylindrical body and a pair of opposing openings opposite the motor, and a pair of holders each disposed in one of the pair of opposing openings, each of the holders having an opening on one end sized to receive a capillary tube. The system further includes a diagnosis device having a graphical screen. The diagnosis device being configured to display a base line indicia, a lower normal line indicia, an upper normal line indicia, and a 100% level line indicia. The lower normal line indicia has a first starting point spaced apart from the base line, the lower normal line extending on an angle relative to the base line. The upper normal line indicia has a second starting point coincident with the first starting point, the upper normal line extending on an angle relative to the lower normal line. The 100% level line indicia has a third starting point spaced apart from the first starting point, the 100% level line extending on an angle relative to the upper normal line.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION

The monitoring of human hematocrit is desirable to diagnose a variety of diseases and disorders. In remote or low resource areas this may be difficult due to the lack of facilities or economic resources to afford the capital equipment typically used for analyzing a patient's hematocrit. Still further issues may arise in these areas in consistent collection of a patient's sample. Embodiments of the present disclosure provide a portable centrifuge that is capable of processing hematocrit operating under battery power or with a renewable energy source. Embodiments of the present disclosure provide advantages in the rapid processing of small quantities of hematocrit. Embodiments of the present disclosure provide advantages in the assessment of a patient's hematocrit for a range of sample volumes. Still further advantages of the present disclosure provide advantages in assessing a patient's hematocrit using a rotor with microfluidic channels and a manually operated centrifuge.

Figure 1:
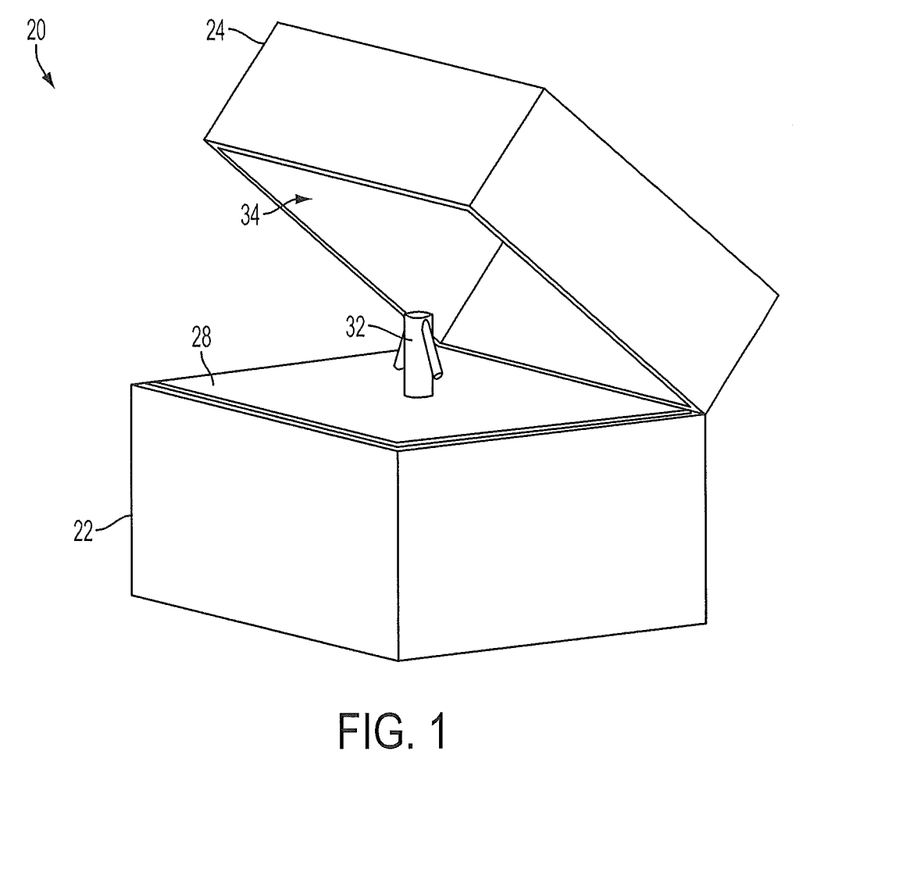
FIG. 1 is a perspective view of a centrifuge in accordance with an embodiment of the invention.
Figure 2:
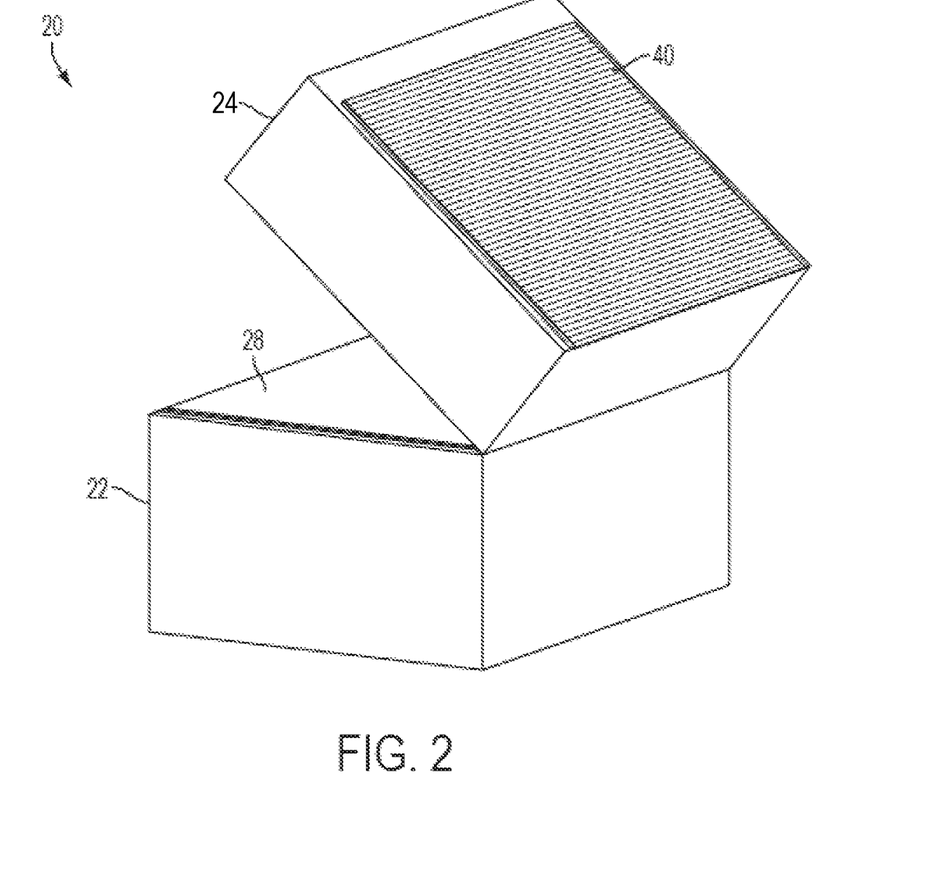
FIG. 2 is another perspective view of the centrifuge of FIG. 1.
Figure 3:
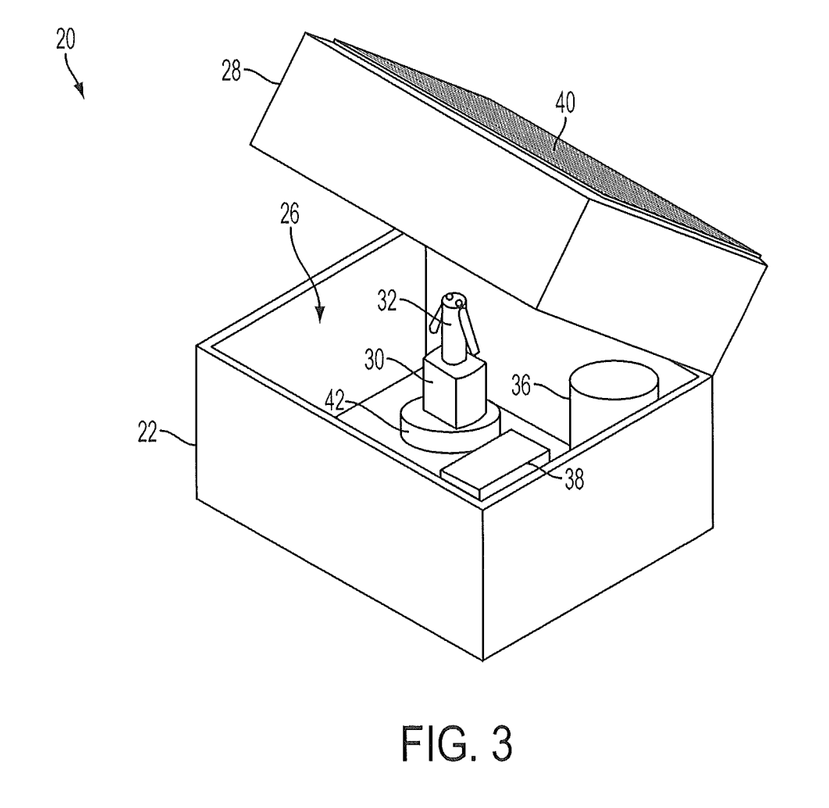
FIG. 3 is another perspective view of the centrifuge of FIG. 1 with a portion of the housing removed.
Figure 4:
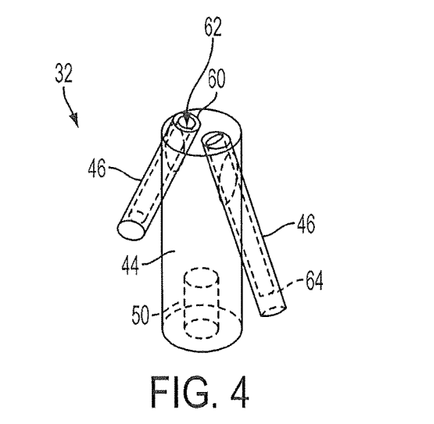
FIGS. 4-7 are views of a rotor for use with the centrifuge of FIG. 1.
Figure 5:
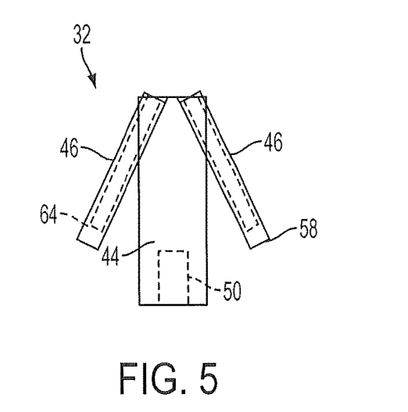
Figure 6:
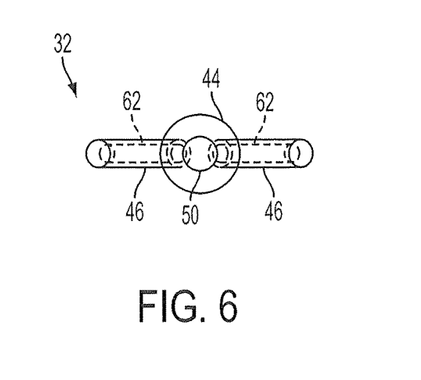
Figure 7:
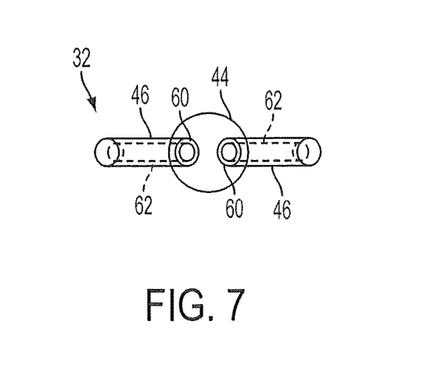
Figure 8A:
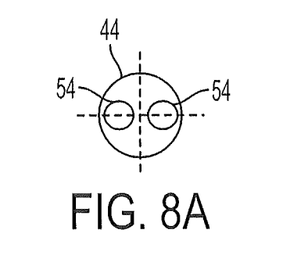
FIGS. 8A-8C are views of the rotor body of FIG. 4.
Figure 8B:
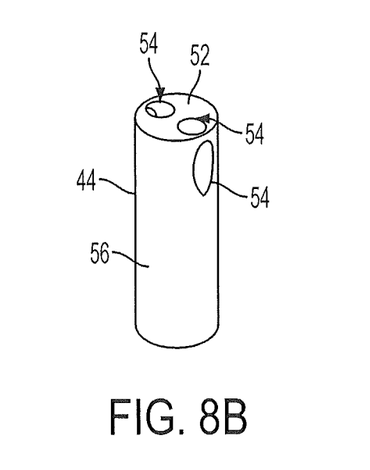
Figure 8C:
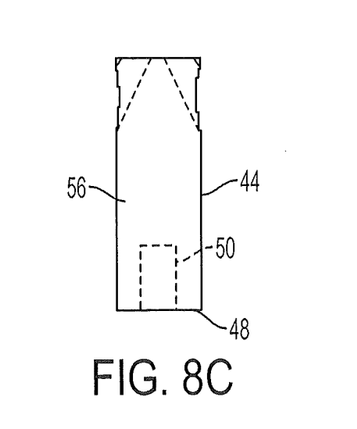

Referring now to FIGS. 1-3, a centrifuge 20 is shown that is configured to operate in remote areas or low resource areas. As used herein, the term "low resource area" refers to a geographic region or area lacking consistent or reliable access to electricity and medical laboratory facilities. A low resource area may also include a trauma surgery amphitheater or a military combat theater. The centrifuge 20 has a base 22 and a cover 24. The cover 24 is rotationally coupled to the base 22 to allow the cover 24 to move from a closed to an open position. In the exemplary embodiment, the base 22 and cover 24 are made from a suitably light weight material such as polystyrene or styrene butadiene methyl methacrylate for example. In one embodiment, the centrifuge 20 may include an interlock switch (not shown) that prevents the operation of the centrifuge 20 when the cover 24 is in the open position.

It should be appreciated that while embodiments herein reference the separation of blood with the centrifuge 20, this is for exemplary purposes and the claimed invention should not be so limited. In other embodiments, the centrifuge 20 may be used to separate other fluids, such as but not limited to fluids having fluid or non-fluid components having different densities, tears, urine, stool, saliva, sweat, or water sources for example.

The base 22 defines a hollow area 26 arranged beneath a base cover 28. The base cover 28 includes an opening that allows a shaft on a motor 30 to extend into a space 34 within the cover 24. The motor 30 is mounted to the base 22, such as with a motor mount 42 for example. The motor mount 42 may be any suitable mounting arrangement that supports the motor 30 and reduces the transfer of vibrations from the motor 30 into the base 22. In the exemplary embodiment, the motor 30 is a 1.5-3V, 12,500 rpm direct current motor, such as a Model ST130-22770-38 motor manufactured by Jency Motor for example. As will be discussed in more detail below, a rotor 32 is coupled to the shaft and rotates within the space 34. In one embodiment, the cover 24 is reinforced act as a containment vessel. In yet another embodiment, the cover 24, the base 22 or the base cover 28 include one or more seals arrangements, such as a gasket for example, that seals the space 34 to prevent the escaping of aerosols from the centrifuge 20 in the event a sample breaks during operation.

Disposed within the hollow area 26 may be one or more components, such as a battery 36 and a controller 38. The battery 36 is electrically connected to a solar panel 40. In one embodiment, the solar panel 40 is mounted to the base cover 28 opposite the space 34. In the exemplary embodiment, the solar panel 40 is comprised of five 1000 mA, 0.55 W solar panels, such as a P-Maxx Series solar cell manufactured by Silicon Solar Inc for example. In one embodiment, each of the individual solar panels 40 are 0.938 inches (23.8 millimeters) wide, 6.125 inches (155.6 millimeters) long and 0.050 inches (1.27 millimeters) thick.

It should be appreciated that while a single battery 36 is shown, this is for exemplary purposes and the claimed invention should not be so limited. The disclosed centrifuge 20 may have multiple batteries arranged in series or in parallel. In one embodiment, the centrifuge 20 has two batteries 36 that are arranged in parallel. In this embodiment, each of the batteries may support operation of the centrifuge individually. This allows the centrifuge 20 to be operated by a first battery 36 while a second battery 36 is being charged by the solar panel 40. In yet another embodiment, the centrifuge may be operated directly by the power generated from solar panel 40.

It should be further appreciated that while the controller 38 is shown as a single component, the control and operation of the centrifuge 20 may be performed by a plurality of individual components, each providing one or more functions, such as but not limited to a motor controller, and a battery charging circuit for example.

Referring now to FIGS. 4-8, the centrifuge rotor 32 is shown that holds hematocrit samples during operation. The rotor 32 includes a body 44 and a pair of opposing holders 46. The body 44 has a generally cylindrical shape. On a first end 48 is a threaded opening 50. The opening 50 is sized and shaped to couple with a shaft on the motor 30. In the exemplary embodiment, the opening 50 has a diameter of 0.08 inches (2.032 millimeters). It should be appreciated that the motor 30 and the body 44 may include additional features (not shown) that keep the rotor 44 centered on the motor 30 shaft, such as matching conical surfaces for example, and also include features that keep the rotor 44 from decoupling under deceleration, such as a pin extending perpendicular to the shaft that is disposed within a slot on the end 48.

Opposite the end 48 is a second end 52. The second end 52 includes a pair of opposing openings 54. Each of openings 54 is formed on an angle and extend through the sidewall 56 of the body 44. In the exemplary embodiment, the openings are formed on a 65 degree angle from a horizontal plane. In the exemplary embodiment, the openings 54 are cylindrical openings. In other embodiments, the openings 54 may have features, such as a step for example, that cooperates with a corresponding feature on the holders 46 to assist in retaining holders 46 in the rotor 32. In the exemplary embodiment, the body is made from a polycarbonate material, has a diameter of about 0.375 inches (9.525 millimeters) and a length of 1.15 inches (29.21 millimeters).

Figure 9:
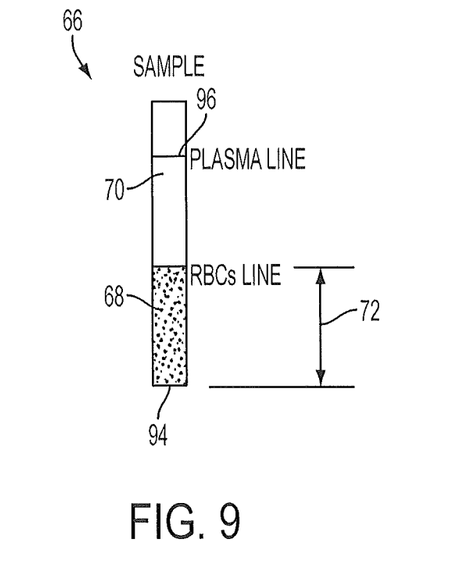
FIG. 9 is a side view of an exemplary capillary tube for use in the rotor of FIG. 4.

The holders 46 are generally cylindrical in shape and having a diameter sized to fit within the openings 54. The holder 46 may be made from a suitable material, such as carbon fiber for example, that is capable of supporting the patient's samples under the centripetal forces generated during operation. Each holder 46 has a first end 58 positioned distal from the sidewall 56. A second end 60 is opposite the first end 58. In one embodiment, the holders 46 have a diameter of 0.125 inches (3.175 millimeters) and a length of 0.9 inches (22.86 millimeters). A blind bore 62 is formed in the end 60 which has a bottom end 64 adjacent the first end 58. The bore 62 is sized to receive a capillary tube 66 (FIG. 9). In the exemplary embodiment, the bore 62 has a diameter of 0.079 inches (2 millimeters) and a length of 0.8 inches (20.32 millimeters). In one embodiment, the holders 46 are bonded to the openings 54 using a suitable adhesive such as cyanoacrylate for example.

In another embodiment, the holders 46 are gradually tapered from a larger diameter at the second end 60 to a smaller diameter at the first end 58. The body 44 has openings 54 with a corresponding taper. In this manner, the holders 46 may be inserted and held in place during operation while also allowing them to be removed for replacement or cleaning. In one embodiment, the rotor 32 is made from materials that are suitable with chemical sterilization or autoclaving.

In operation, the centrifuge 20 is installed in a location where the solar panel 40 is exposed to sun and the batteries 36 are charged. It should be appreciated that solar panel 40 may be removed from the cover 24 and positioned in an environment where sunlight is available, or the centrifuge itself may be placed in the sunlight. Once the batteries 36 are charged to allow operation of the centrifuge, the clinician or other medical personnel obtains a sample of blood from a patient in a capillary tube 66 sized to fit within the bore 62. The capillary tube 66 is inserted into the centrifuge 20. Typically, two capillary tubes 66 will be processed at the same time to maintain a balanced rotor 32. In the event that only one sample needs to be processed, the clinician may insert an equally weighted capillary tube with an inert material (e.g. saline) in the opposing holder 46.

With the capillary tubes 66 inserted, the cover 24 is closed and the rotor is rotated for a desired period of time. In the exemplary embodiment, the samples are processed for at a speed of 10,000 rpm for 90 seconds. The rotation of the capillary tubes 66 causes the sample to separate into a first portion 68 containing red blood cells and a second portion 70 containing plasma. In the sample volumes used to check hematocrit, the buffy layer while present is negligible. With the sample separated into its components, the clinician may then measure the height 72 of the first portion 68 to determine if the patient's hematocrit is within the normal range, or if the patient is anemic or polycythemic.

One problem in remote and low resource areas is controlling the quantity of blood placed in the capillary tube 66. Typical conventional hematocrit procedures simply measure the height of the red blood cell column and assume that a standardized level of blood was obtained from the patient. As a result, the diagnosis made from reading the hematocrit may be erroneous if too large or too small of a sample is used.

Figure 10:
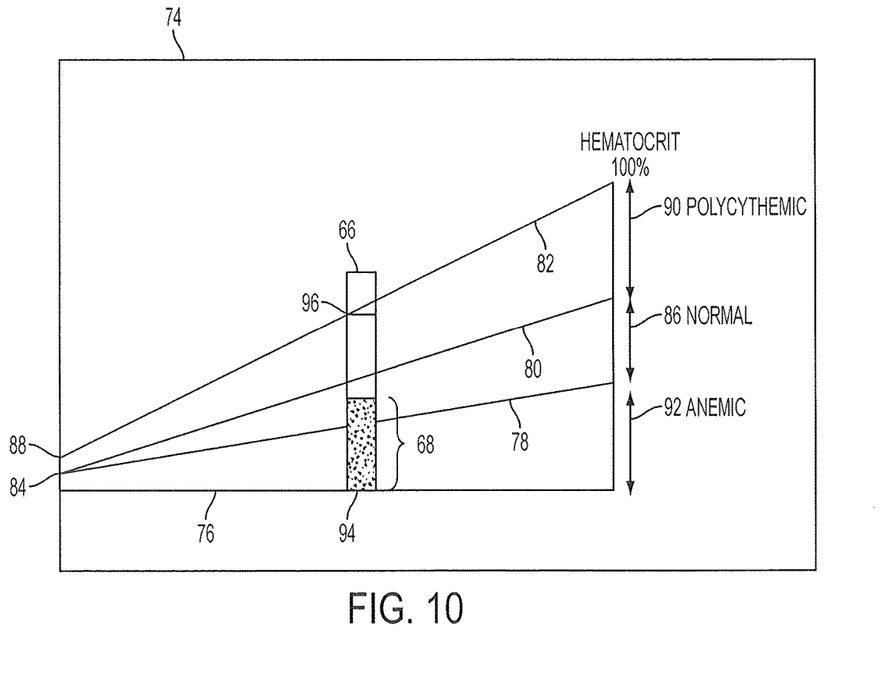
FIG. 10 is a hematocrit card for use with the capillary tube of FIG. 9.

In one embodiment, a diagnosis card 74 is provided that assists the clinician in diagnosing the patient by having indicia that indicate different conditions. The card 74 has a series of lines, including a base line 76, a lower normal range line 78, an upper normal range line 80 and a 100% level line 82. The lines 78, 80 start at a common point 84 and extend on an angle, diverging as the line proceeds from the left side of the card to the right. The diverging lines 78, 80 define the normal range 86 of red blood cells. The 100% level line 82 starts from a point 88 spaced apart from the point 84 and extends on an angle as the line extends from the left side to the right side. The area between the upper normal range line 80 and the plasma line 96 defines a polycythemic range 90. Similarly, the area 94 between the lower normal range line 78 and the base line 76 defines the anemic range 92.

Typically, different demographics of patients will have different diagnosis cards. For example, an infant will not have the same normal range as an adult. In one embodiment, the diagnosis card may have indicia representing different demographic groups. In this embodiment, each demographic group may be differentiated by having lines of different colors. In one embodiment, the diagnosis card may include lines for an adult male, an adult female, a ten year old adolescent, a one year old child and a three month old child.

The diagnosis card 74 may be made from a suitable material for the environment in which it will be used, such as but not limited to paper, card stock, card board, corrugated card board, wood, plastic or metal for example. The diagnosis card 74 may be laminated with a clear plastic. In one embodiment, the diagnosis card 74 is a graphical representation on an electronic computing device having a screen or a monitor capable of displaying the graphical representation of the diagnosis card 74, such as but not limited to a computer, a laptop, a personal digital assistant, a tablet device, a telephone, a cellular phone, an internet phone or an e-reader device for example.

To use the diagnosis card 74, the clinician processes the capillary tube 66 to separate the red blood cells from the plasma as described above. The clinician then places the capillary tube 66 against the card 74 with the bottom of the capillary tube 66 on the base line 76. The capillary tube 66 is then moved along the base line 76 until the plasma line 96 intersects the 100% level line. With the capillary tube 66 in this position, the clinician may then determine if the patient is within normal, anemic or polycythemic ranges. It should be appreciated that the angling of the lines 78, 80, 82 allows for scalability in the sample levels that are processed, providing advantages in increasing the accuracy of the diagnosis. It should further be appreciated that the diagnosis card 74, since it does not rely upon measurements with a ruler or other device, may be easier for less skilled personnel, or personnel operating in a turbulent environment (e.g. a military field hospital), to use. In one embodiment, the ranges 86, 90, 92 may be color coded to facilitate usage to by personnel who may be illiterate or have poor reading skills.

In one embodiment, the clinician may take a digital photograph of the diagnosis card 74 with an electronic device such as but not limited to a digital camera, a cellular phone, a tablet device or a laptop for example. The electronic computing device may then scale the photograph to automatically, or through manual adjustment by the user, line up the image of the capillary tube 66 on a graphical representation of the diagnosis card 74. In still another embodiment, the electronic computer device may automatically detect the level 68 and the plasma line 96 and determine whether the hematocrit is within the normal, anemic or polycythemic ranges.

Figure 11:
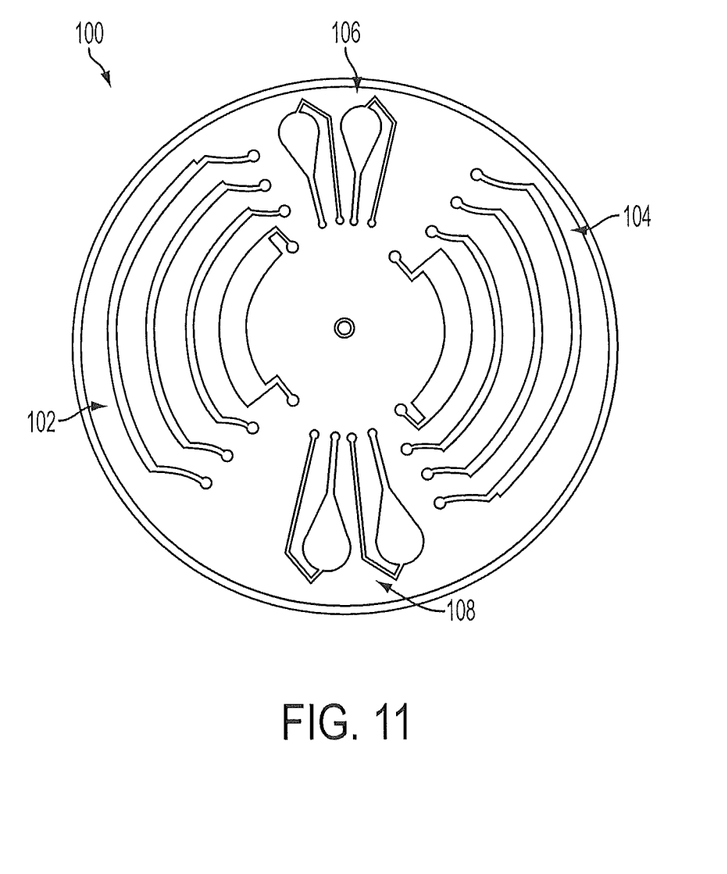
FIG. 11 is a top view of a centrifuge rotor having microfluidic channels.
Figure 12:
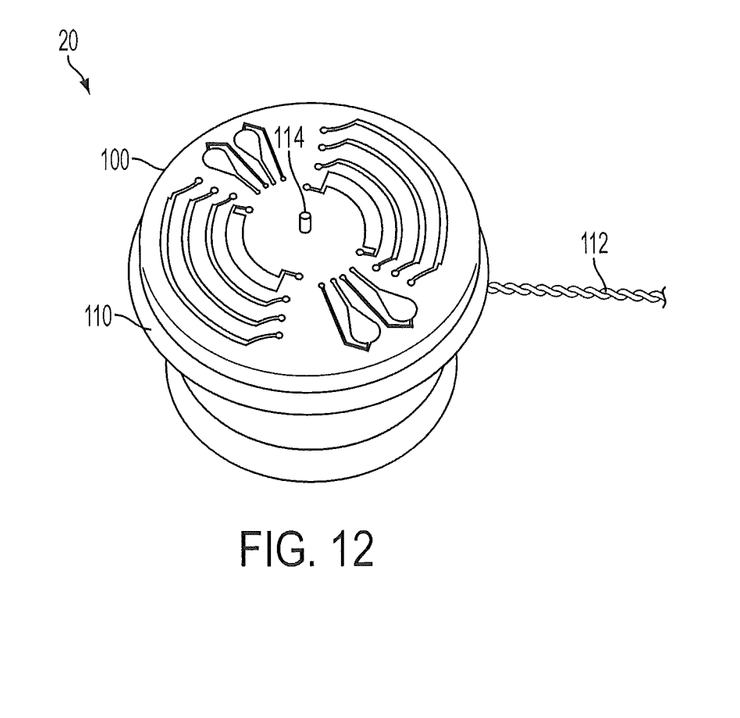
FIG. 12 is a perspective view of a manually operated centrifuge for use with the rotor of FIG. 11.

Referring now to FIGS. 11-12, another embodiment is shown of the centrifuge 20 for use in low resource or remote locations. In this embodiment, the blood sample is loaded into a rotor 100 in the form of a disk having a plurality of microfluidic channels 102, 104, 106, 108. This arrangement provides for even smaller volumes of sample from the patient and may lead to faster separation of the red blood cells and plasma. This may provide still further advantages in having a manually operated centrifuge 20 as shown in FIG. 11. In this embodiment, the rotor 100 is coupled to device 110 that is similar to a yoyo having a string 112 wrapped around a center axis 114. To rotate the rotor 100, the clinician simply pulls the string 112 causing the device 110 and the rotor 100 to spin. In one embodiment, the clinician may spin the rotor 100 multiple times to achieve the desired separation.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of evaluating a patient's hematocrit comprising:
    collecting a sample of blood in a capillary tube;
    placing the capillary tube into a centrifuge having a rotor, the centrifuge having a base and a lid pivotally coupled to the base and movable between a closed and an open position, the lid defining a space, the centrifuge further having a power source disposed within the base and configured to generate electrical power from a renewable power source and at least one battery electrically coupled to the power source, the centrifuge further having a motor disposed within the base and electrically coupled to the at least one battery, wherein the rotor is disposed within the space and removably coupled to the motor when the lid is in the open position, the rotor having a bottom end coupled to the motor, the rotor having a generally cylindrical body and a pair of opposing openings on a top surface opposite the motor, and a pair of holders each disposed in one of the pair of opposing openings, each of the pair of holders having an opening on a first end sized to receive the capillary tube, wherein each of the pair of holders extends from the top surface through a side of the cylindrical body, a second end of each of the pair of holders being spaced apart from the side and being vertically disposed above the bottom end, wherein at least a portion of each of the pair of holders extends directly into the space;
    separating the sample of blood with the centrifuge into a red blood cell portion and a plasma portion;
    displaying on a graphical screen of an electronic diagnosis device a first image, image having a first size and scale, the first image comprising:
        a base line indicia;
        a lower normal line indicia having a first starting point spaced apart from the base line indicia, the lower normal line indicia extending on a first angle relative to the base line indicia;
        an upper normal line indicia having a second starting point coincident with the first starting point, the upper normal line indicia extending on a second angle relative to the lower normal line indicia;
        a 100% level line indicia having a third starting point spaced apart from the first starting point, the 100% level line indicia extending on a third angle relative to the upper normal line indicia; and
    determining a patients hematocrit based on the separated blood sample and the first image;
    wherein the base line indicia, the lower normal line indicia, the upper normal line indicia, and the 100% level line indicia are selected and displayed based on demographic information of the patient.

2. The method of claim 1 wherein the renewable energy source includes a solar panel coupled to the lid.

3. The method of claim 1 further comprising acquiring a second image of the separated blood sample with the diagnostic device, the second image having a second size and scale, wherein the second image is a digital photograph.

4. The method of claim 3 further comprising changing with the diagnostic device the second size and scale to match the first size and scale.

5. The method of claim 4 further comprising superimposing the second image on the first image at the graphical screen of the electronic diagnosis device.

6. The method of claim 5 wherein the diagnostic device is an electronic computer device.

7. The method of claim 6 further comprising determining with the electronic computer device, a first edge of the red blood cell portion and a second edge of the plasma portion in the second image.

* * * * *